United States Patent [19]

Mallia, Jr.

[11] Patent Number: 5,614,107
[45] Date of Patent: Mar. 25, 1997

[54] METHOD OF FREEZE DRYING SEWAGE SLUDGE

[75] Inventor: Albert T. Mallia, Jr., Pocono Pines, Pa.

[73] Assignee: Enviro-Tech-2000, Inc., Scotrun, Pa.

[21] Appl. No.: 543,037

[22] Filed: Oct. 13, 1995

[51] Int. Cl.$^6$ .................. C02F 1/22; C02F 1/12
[52] U.S. Cl. .......... 210/771; 210/774; 210/808; 34/292; 241/20; 239/2.2; 159/47.3; 159/905; 159/DIG. 5; 159/DIG. 16; 203/DIG. 5
[58] Field of Search ................ 34/92, 287, 289, 34/292, 293, 298; 210/768, 770, 771, 774, 808; 241/20; 239/2.2; 165/111, 112; 159/905, DIG. 5, DIG. 16, 47.3; 203/DIG. 5, 91

[56] References Cited

U.S. PATENT DOCUMENTS

| | | |
|---|---|---|
| 3,677,405 | 7/1972 | Keith, Jr. . |
| 3,714,792 | 2/1973 | Murphy et al. . |
| 3,745,782 | 7/1973 | Neyhart et al. . |
| 3,817,048 | 6/1974 | Burley . |
| 3,880,756 | 4/1975 | Raineri et al. . |
| 4,787,970 | 11/1988 | Sutphen . |
| 5,202,034 | 4/1993 | Martel, Jr. .............. 210/770 |
| 5,250,192 | 10/1993 | Martel, Jr. .............. 210/737 |

OTHER PUBLICATIONS

"Popular Science" Magazine, Dec. 1995, p. 42, an article entitled Pure as Snow.

*Primary Examiner*—Robert J. Popovics
*Attorney, Agent, or Firm*—Jonathan A. Bay

[57] ABSTRACT

A method for processing sewage eliminates chemical "treatment", or, the addition of chemicals that are as harmful or more so to the environment as raw sewage. The method of processing sewage disintegrates the generally solid components of sewage into a highly de-moisturized powder via alternative processes of either (i) a freeze-drying process, or (ii) a combination centrifugal separation and an evacuated "bake-out" process, both which substantially drive out the vaporizable components of the sewage. In consequence, there are no resultant effluent and/or exhausting vapors from this method which would impact the environment.

13 Claims, 5 Drawing Sheets

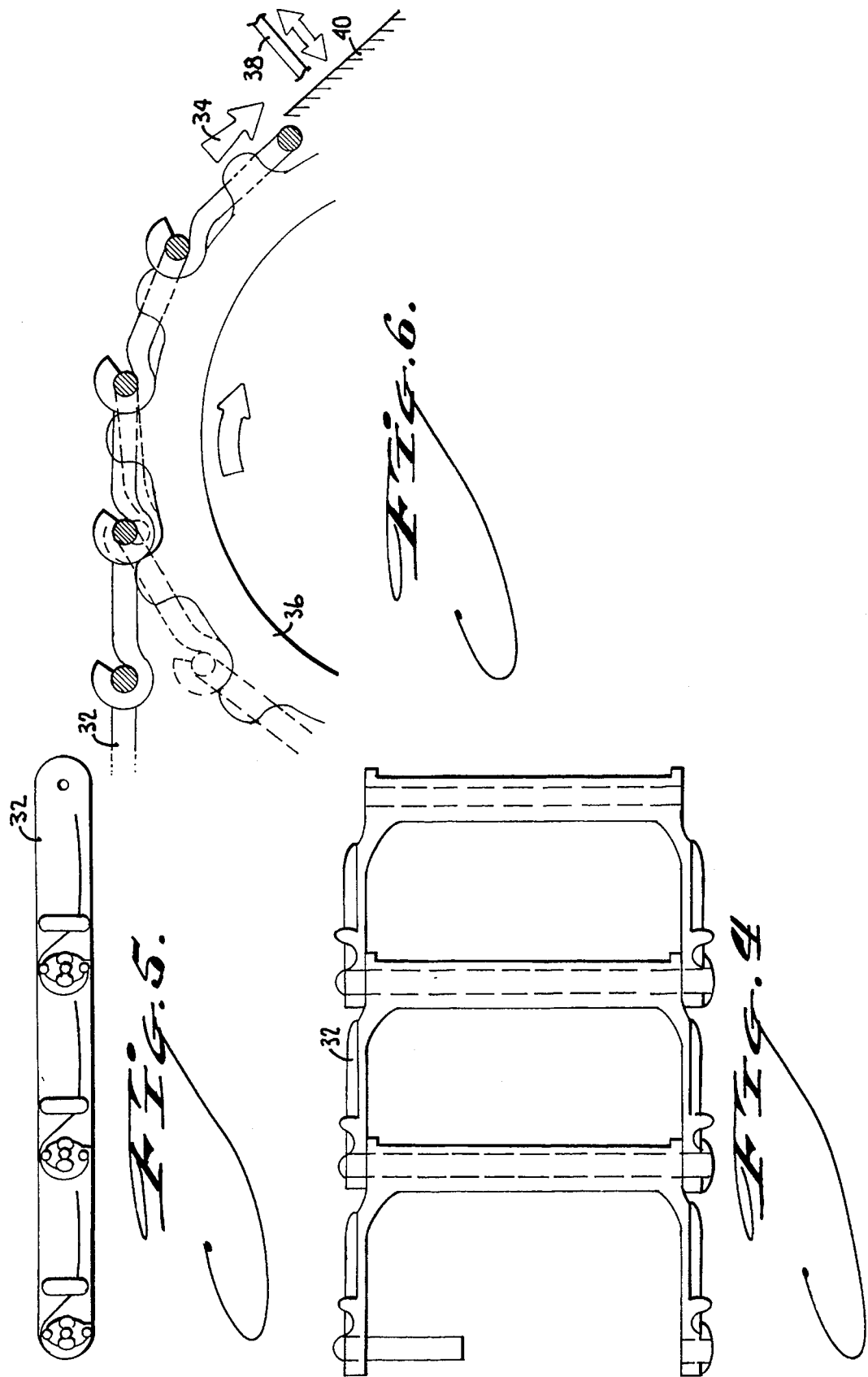

METHOD OF FREEZE DRYING SEWAGE SLUDGE

BACKGROUND OF THE INVENTION

1. Field of the Invention

The invention relates to a method of processing sewage, as distinguished from "treating" sewage. "Treating" sewage generally entails adding chemicals to the sewage. During treatment, chemicals generally neutralize the effluent to return to the environment as the waterways and atmosphere and the like. Processing sewage in accordance with the invention entails vaporizing the vaporizable components of the sewage while disintegrating the solid components via a freeze-drying process or a combination centrifugal separation and evacuated "bake-out" process, and so on.

2. Prior Art

The popular method for handling sewage in sewage plants entails "treating" the sewage with relatively expensive chemicals. There are several shortcomings associated with treating sewage via chemicals. The chemicals that are added during treatment are generally considered hazardous to the environment, i.e., they "impact" the air and waterways. Thus it is inefficient to add chemicals to treat sewage in order to comply with governmental environmental regulations. Moreover, chemically treating sewage sometimes resulting a failure to safely neutralize the effluent. The usual response is to increase the relative proportions of chemicals added. The sewage plants consequently use more chemicals of which some proportion leaks to the environment. And as sewage production increases because of increased housing or commercial development, still more chemicals are used to meet the growth.

The baseline problem is that these chemicals are expensive. The named-inventor hereof has information and belief that a sewage treatment plant in Harrisburg, Pa. incurs a $360 thousand dollar annual expense for the chemicals it uses.

Another shortcoming associated with the popularly-known sewage treatment plants is their reliance on leach "fields", i.e., shallow ponds or lagoons. The relatively larger sewage treatment plants can be found with several hundreds of the surrounding acres converted into leach fields in which the effluent of the plant is percolated as a step in the treatment to disintegrate/eliminate hazardous components of the effluent, some of which hazardous components were generated by the chemical treating method.

It would be a desirable improvement in sewage handling, if the addition of chemicals could be eliminated. It would also be a desirable improvement in sewage handling if the leach fields could likewise be eliminated. What is needed is a method of processing sewage which eliminates chemical treating and leach fields, and otherwise overcomes the shortcomings of the prior art.

SUMMARY OF THE INVENTION

It is an object of the invention to provide a method for processing sewage via a process which eliminates treating the sewage with chemicals and thereby not "impact" the environment.

It is another object of the invention that the above process eliminate the leach fields associated with the present chemical treatments of sewage.

It is an additional object of the invention to disintegrate the generally solid components of the sewage into a crumbly, flaky, highly de-moisturized residue.

It is a further object of the invention to attain the above highly de-moisturized residue via a given vaporizing process chosen from one of a freeze-drying process, or a combination centrifugal separation and evacuated "bake-out" process, and so on.

It is still another object of the invention to bag the end-product, highly de-moisturized residue in a continuous succession of heat-sealable plastic liners for convenience in removal off-site and distribution to end-users such as purchasers of bags of fertilizer and the like.

These and other aspects and objects are provided according to the invention in a method for processing sewage which, in accordance with one embodiment, comprises the following steps. An infeed of sewage is fed to a grinder that grinds the sewage into a relatively finely-ground liquid suspension. The liquid suspension is then throughputted through a booster pump to boost a line pressure thereof. The pressure-boosted liquid suspension is next supplied to a manifold of throttling nozzles that are arranged to discharge into a freezing atmosphere maintained at a given freezing temperature chosen so that the throttled liquid suspension forms into icy granular particles. A vacuum is next drawn over the icy granular particles and then the icy granular particles are subjects to a step of vaporizing the generally vaporizable components of the icy granular particles. The combined effects of evacuation and vaporization operate to disintegrate the generally solid components into a freeze-dried, highly-de-moisturized crumbly residue. The generally vaporizable components are preferably exhausted to a condenser. The freeze-dried residue is in a form that is suitable for convenient off-site removal, and revenue-producing distribution such as exploitation as fertilizer.

In accordance with another embodiment of the invention, the above steps of boosting the line pressure, freezing, evacuating and vaporizing, are replaced by the following steps. The finely-ground liquid suspension is ted to a centrifugal separator that separates the liquid suspension into a (i) thickened liquid suspension and (i) vapor, which vapor constitutes only portions of the sum-total content of the generally vaporizable components of the sewage. The vapor in the centrifugal separator is preferably exhausted to a condenser. Next a vacuum is drawn over the thickened liquid suspension, which is then subjected to a step of vaporizing the remainder portions of the generally vaporizable components within the thickened liquid suspension. These combined steps operate to disintegrate the generally solid components of the sewage into a crumbly, highly de-moisturized residue.

Other inventive aspects of the method in accordance with the invention optionally comprise the following.

For example, the step of freezing the throttle discharge might preferably comprise providing a freezer chamber for enclosing the freezing atmosphere. Similarly, there likely would be a vacuum chamber in which occurs the step of drawing a vacuum. There naturally would be intercommunicating conduits and/or conveyors between the two chambers.

The step of can comprise at least one of the following methods of accomplishing the desired result, namely either heating, irradiating, and/or microwaving. Also, before grinding the sewage in the grinding pump, it makes sense with certain infeeds of sewage to place a settling tank or like separator before the grinding pump in order to eliminate from the infeed of sewage, non-grindable entrained particles as metallic objects.

The step of exhausting the vapors might more particularly comprise a step of extracting a condensate from portions of the vapors. The condensate has certain beneficial and revenue-producing uses, such as sprinkling lawns or supplying fire hydrants, and/or the condensate can be recycled through the tanks in water closets in which the infeed of sewage most probably originated. In addition, those portions of the vapors which do not condense have other beneficial and revenue-producing uses, such as incinerating or combusting for generating heat or electric power.

A number of additional features and objects will be apparent in connection with the following discussion of preferred embodiments and examples.

BRIEF DESCRIPTION OF THE DRAWINGS

There are shown in the drawings certain exemplary embodiments of the invention as presently preferred. It should be understood that the invention is not limited to the embodiments disclosed as examples, and is capable of variation within the scope of the appended claims. In the drawings.

FIG. 4 is a plan view of a scraper-type flight conveyor that is deployed in various tanks and/or chambers of the sewage process plant;

FIG. 5 is a side elevational view thereof;

FIG. 6 is a side elevational view, partly broken away, showing both a drive sprocket of the above flight conveyor and an reversibly closable outlet door of a chamber enclosing the flight conveyor in its entirety;

DETAILED DESCRIPTION OF THE PREFERRED EMBODIMENTS

Figure 1:
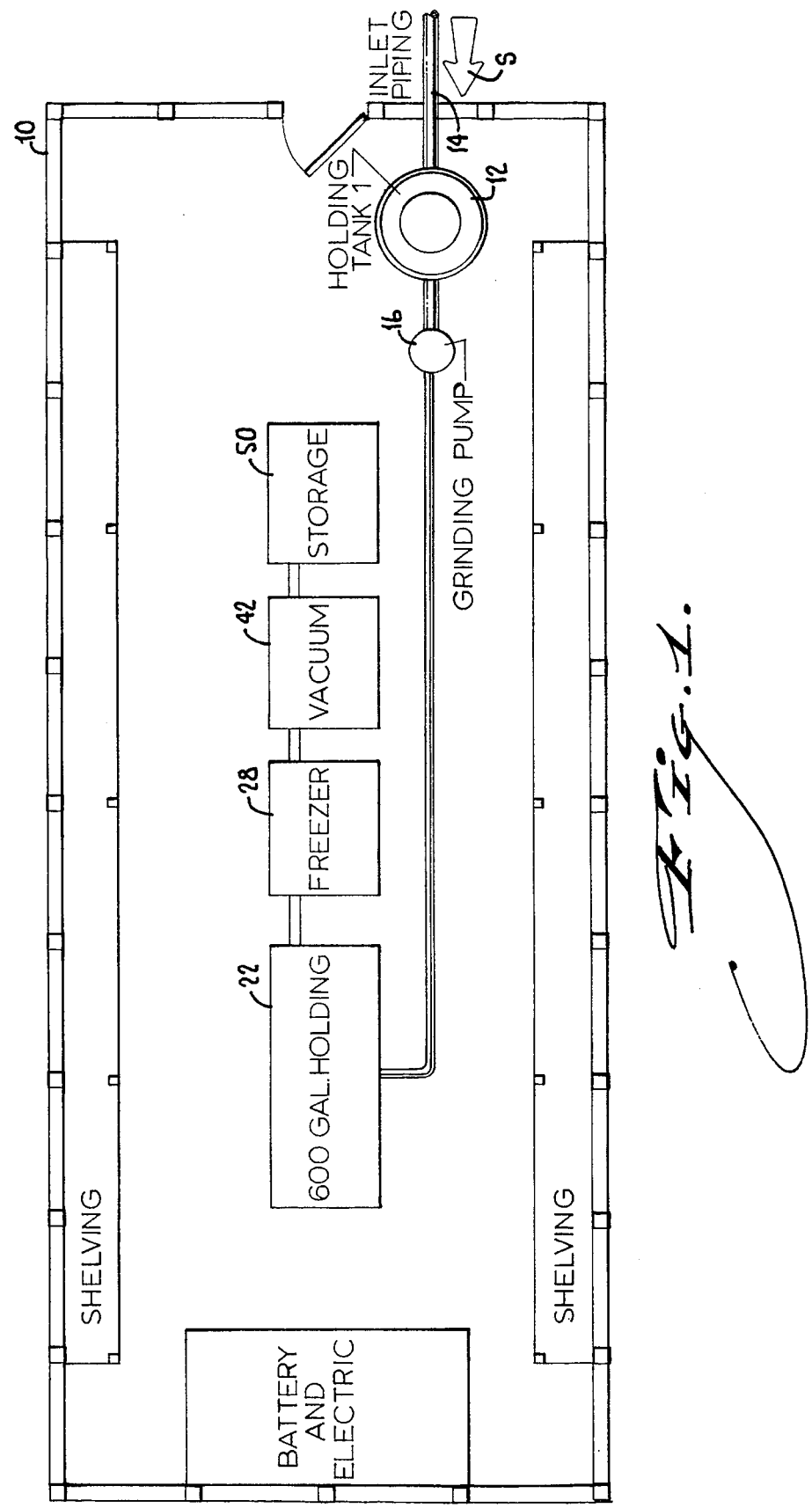
FIG. 1 is a plan view of a sewage process plant for carrying out a method of processing sewage in accordance with the invention.
Figure 2:
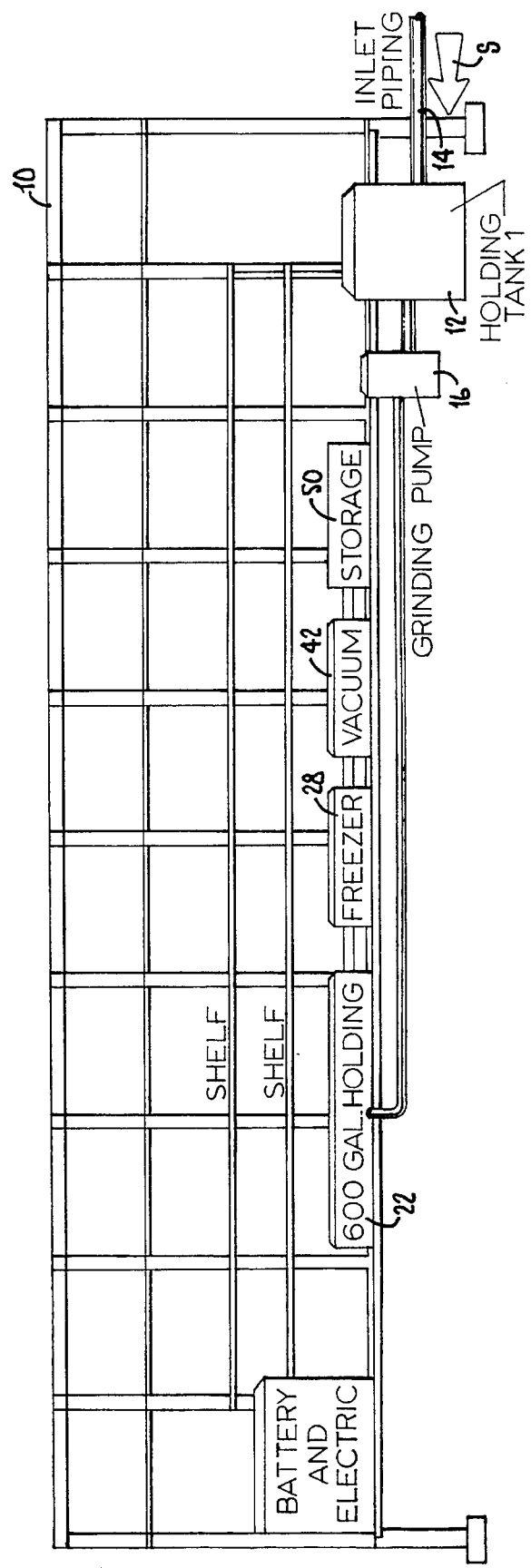
FIG. 2 is a side elevational view thereof.
Figure 3:
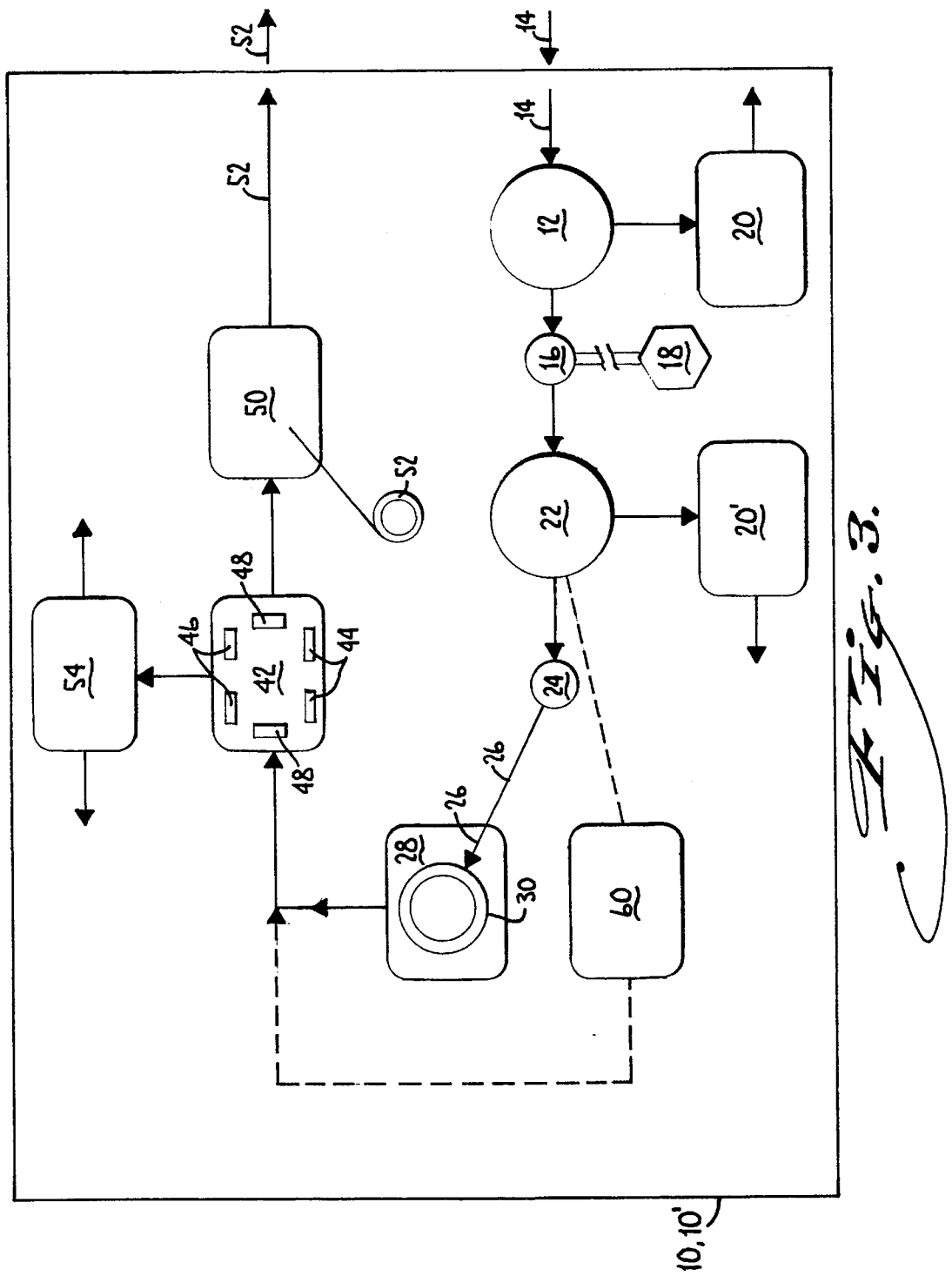
FIG. 3 is a flow chart that diagrammatically depicts components of the sewage process plant of FIG. 1.

FIGS. 1 and 2 show a sewage process plant 10 for carrying out a method of sewage processing in accordance with the invention. With further reference to FIG. 3, the sewage process plant 10 optionally comprises the following components for processing sewage S as that typically has generally solid components and generally vaporizable components, including much water.

A settling/holding tank 12 is supplied with an infeed of sewage S via inlet piping 14. The size of the settling tank 12, as is true with all other parts of the sewage process plant 10, varies with the intended sewage-carrying capacity for which the plant 10 is designed. The plant 10 can be sized to handle the sewage output of a single residential dwelling. Or the plant 10 can be enlarged as needed to handle increased sewage capacities as, for example, the output of a community of residential dwellings, or even a larger community of mixed residential and commercial properties. It is also known to haul sewage in trucks from remote sites, including farms, and unload the sewage to the sewage process plant 10. Thus the size of the plant 10 can be varied as desired. The particular size of any plant for carrying out the method(s) described here in this description is not limiting to the method in accordance with the invention.

The inlet piping 14 terminates in the settling/holding tank 12, which is drained by a grinding pump 16. The settling/holding tank 12 operates to settle out certain entrained non-grindable objects as metallic objects and the like (not shown), because these objects will damage the impellers (not shown) of the grinding pump 16. The metal objects are removed from inside the tank 12 by "scraper-type" flight conveyors, as are more particularly described below, or other suitable means. The settling/holding tank 12 also operates to collect sufficient sewage S until the sewage reaches a level in the tank 12 to make operation of the plant 10 more optimally efficient. The plant 10 can shut down for periods when the sewage merely trickles in, to switch on when sufficient sewage has collected to make processing a batch feasible. Control of the plant can be accomplished via a microprocessor 18 and the like. The settling/holding tank 12 is ventilated by a system 20 that draws off the vapors and processes then for relatively valuable components as methane.

As previously stated, this sewage process plant 10 is preferably remotely operable by a microprocessor 18 that, among other tasks, switches the grinding pump 16 on and off on depending on the levels of the sewage S in the holding/settling tank 12. The grinding pump 16 preferably finely grinds the sewage into a liquid suspension as a "puree" of sorts. Grinding pumps of this type for sewage are commercially available from such producers as, for example, F. E. Myers Company in Ashland, Ohio. The grinding pump 16 outputs to a holding tank 22, relatively smaller than the settling/holding tank 12 on the suction-side of the grinding pump 16, for accumulating a reservoir/or the suction-side of a booster pump 24. This holding tank 22 is also ventilated by a system 20' that draws off the vapors and processes them for relatively valuable components as methane.

The booster pump 24 preferably increases a line pressure of an outlet line 26 to a substantial pressure as 150 psig (psi gauge) or the like. The outlet line 26 extends into an interior of a freezer chamber 28 and terminates in a manifold of throttling nozzles 30. The throttling nozzles 30 discharge the liquid suspension (i.e., the finely ground sewage) into a freezing atmosphere in the freezer chamber 28 that is chilled to a freezing temperature sufficient to transform the spray into a "snow/fall" of icy granular particles. Exemplary freezing temperatures would range between −10 and −40 degrees Celsius. The icy granular particles settle onto a floor (not shown) of the freezer chamber 28 and are conveyed out of the freezer chamber 28 by a "scraper-type" flight conveyor, as more particularly described next.

FIGS. 4 and 5 depict the scraper flight conveyor 32 that wipes the icy granular particles along the floor of the freezer chamber 28 in a direction to an outlet 34 (the outlet 34 being shown in FIG. 6). In FIG. 6, the outlet 34 comprises a sprocket 36 (either an idler or drive sprocket) for the flight conveyor 32 and a remotely openable and closable door 38. The sprocket 36 defines a terminus of the horizontal flight of the flight conveyor 32. The flight conveyor 32 is preferably entirely enclosed with the freezer chamber 28. As the icy granular particles approach and travel over the sprocket 36, they avalanche into an inclined chute 40 that terminates in a vacuum chamber 42 (FIGS. 1, 2 and 3). The freezer chamber 28 is given the openable and closable door 38 (FIG. 6) to keep inside as much of the freezing atmosphere as possible. The inlet-side of the vacuum chamber 42 has a similarly operative door (not shown) for accepting the avalanching icy granular particles. The vacuum chamber 42 also has a similarly enclosed "scraper" flight conveyor, outlet door, and avalanching inclined outlet chute (all not shown) as the freezer chamber 28.

In the vacuum chamber 42, a vacuum is drawn down over the icy granular particles. The vacuum assists vaporization because of course the relative energy needed to vaporize a vaporizable component generally decreases with decreasing pressure. The generally vaporizable components are vaporized by any given means suitable for the purpose, as baking via convection heaters 44 and/or radiation heaters 46, or other forms of irradiation as micowaving via a microwave generator 48, and the like. As a result of the step(s) of evacuating and vaporizing, the generally solid components of the sewage are reduced or disintegrated into a freeze-dried, crumbly residue. Preferably this freeze-dried crumbly residue is exposed to a dosage of bacteria-killing radiation such as microwaves or the like, as a preferred precaution, before removal out of the sewage plant. This dosage bacteria-killing radiation is preferably applied inside the vacuum chamber by the microwave generator 48.

The freeze-dried crumbly residue is conveyed and avalanched out of the vacuum chamber 42 by the enclosed flight conveyor (compare FIG. 6) via a comparable inclined chute to a bagging station 50. At the bagging station 50, the freeze-dried crumbly reside pours into a continuous succession of bags or plastic liners 52 that are adapted for "welding" or heat sealing to give a sealed plastic liner 52 filled with a load of freeze-dried residue of the sewage process plant 10 in accordance with the invention. This freeze-dried residue has various beneficial and commercially exploitable uses, foremost being its use as fertilizer and the like.

The vapors that are vaporized out of the sewage in the vacuum chamber are drawn out of the vacuum chamber 42 via an evacuated condenser 54 that is evacuated to an even higher vacuum (i.e., relatively lower pressure) than the vacuum chamber 42. The condenser 54 partly condenses portions of the vaporizable components into a condensate. This condensate comprises mainly water. The condensate output of the sewage process plant 10 in accordance with the invention has other beneficial and revenue-generating uses, such as use in lawn-sprinkling systems or fire hydrant systems, or as recycling through the tanks in the water closets in which the sewage originated.

The other portions of the vapors which do not condense partly comprise volatile components which optionally might be mixed with components of the vapors ventilated and collected off the holding tanks by the ventilation/collections systems 20 and 20'. The volatile components might be incinerated or combusted to generate exploitable heat or electric-power. This would reduce the power consumption requirements of the sewage process plant 10 in accordance with the invention that must be drawn from public-utility supplied electric hook-up's and the like. It is presumed that the residual vapors as methane have beneficial and revenue-generating uses that make its collection and containerization for removal off-site in containers both feasible and desirable.

Figure 8:
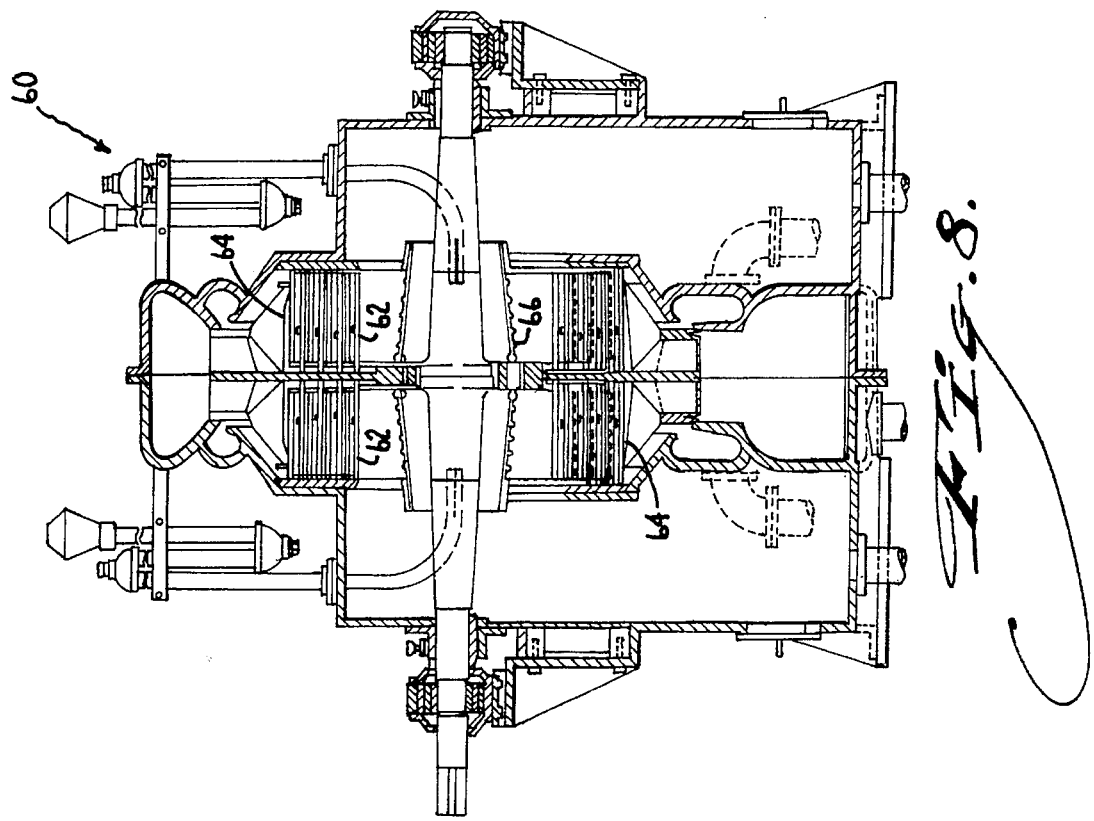
Figure 7:
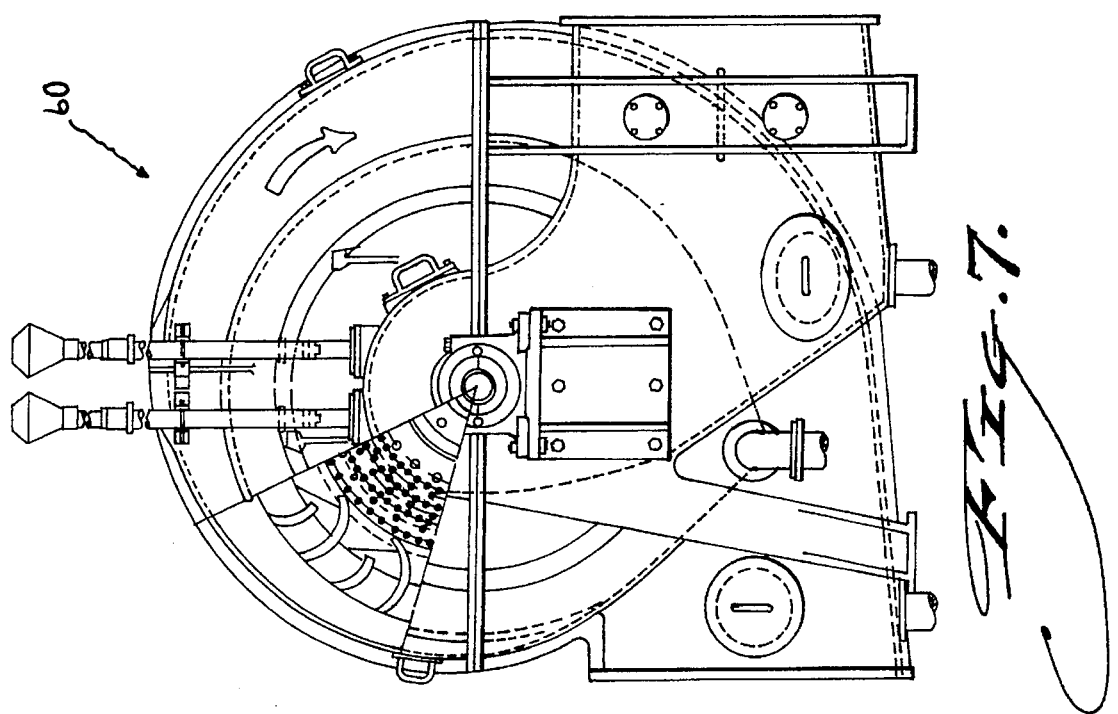
FIG. 7 is an axial, side elevational view, partly broken away, of a "Theisen"-type centrifugal separator: and, FIG. 8 is a vertical, partial sectional view thereof, taken through the rotary axis.

To return to FIG. 3, it shows in broken lines a centrifugal separator 60. The centrifugal separator 60 is disclosed as a component of an alternative embodiment of a sewage process plant 10' for carrying out the method in accordance with the invention. The centrifugal separator 60 is substituted—in this alternative embodiment—for the booster pump 24 and freezer chamber 28 of the previous embodiment. FIGS. 7 and 8 show a known centrifugal separator 60 commonly denominated as a "Theisen disintegrator." The Theisen disintegrator 60 comprises a substantial cast-iron casing enclosing two stationary baskets 62 and one motor-driven rotor basket 64. The liquid suspension (i.e., the finely ground sewage) is injected into, or drained by gravity into, the center of perforated cones 66. Centrifugal force distributes the liquid suspension over a bar system 68. The rotation separates substantial portions of the generally vaporizable components and thickens the other portions of the liquid suspension. The thickened liquid suspension is conveyed to the vacuum chamber 42 as the vaporized portions are drawn out by the evacuated condenser 54. The subsequent evacuating and further vaporizing of the thickened liquid suspension occurs much as described above with the previous embodiment. The resultant solid material is the crumbly form of the generally solid components, much like that obtained from the freeze-drying process.

The invention having been disclosed in connection with the foregoing variations and examples, additional variations will now be apparent to persons skilled in the art. The invention is not intended to be limited to the variations specifically mentioned, and accordingly reference should be made to the appended claims rather than the foregoing discussion of preferred examples, to assess the scope of the invention in which exclusive rights are claimed.

I claim:

1. A method for processing sewage which comprises generally solid components as well as generally vaporizable components, the method comprising the steps of:

grinding an infeed of sewage into a liquid suspension;

pumping the liquid suspension to boost a line pressure thereof;

providing a freezing atmosphere;

throttling the liquid suspension into the freezing atmosphere that is at a given freezing temperature chosen so that the throttled liquid suspension forms into icy granular particles;

and then, to occur substantially close after the occurrence of that last step of throttling:

drawing a vacuum over the icy granular particles and vaporizing the generally vaporizable components of the icy granular particles, which disintegrates the generally solid components into a freeze-dried, crumbly residue;

exhausting the generally vaporizable components to a condenser; and, removing the freeze-dried residue.

2. The method of claim 1, wherein the step of removing the freeze-dried residue further comprises feeding the freeze-dried residue to a bagging station where the freeze-dried residue is poured into and sealed shut in a continuous succession of heat-sealable plastic liners.

3. The method of claim 1, further comprising providing a freezer chamber for enclosing the freezing atmosphere, a vacuum chamber in which occurs the step of drawing a vacuum over the icy granular particles, and, means for conveying the icy granular particles from the freezer chamber to the vacuum chamber.

4. The method of claim 1, wherein the step of throttling comprises discharging the liquid suspension through a manifold of nozzles.

5. The method of claim 1, wherein the step of vaporizing comprises at least one of heating, irradiating, and microwaving.

6. The method of claim 1, further comprising, before the step of grinding, separating from the infeed of sewage non-grindable entrained particles as metallic objects.

7. The method of claim 1, wherein the step of exhausting the generally vaporizable components to the condenser further comprises extracting a condensate from portions of the generally vaporizable components.

8. The method of claim 7, further comprising using the condensate for a given use chosen from one of sprinkling lawns, supplying fire hydrants, and recycling through the tanks in water closets in which the infeed of sewage originated.

9. The method of claim 7, further comprising using the other portions of the generally vaporizable components, which were not condensed, for a given use chosen from one of generating heat and generating electric power.

10. The method of claim 1, wherein the step of removing the freeze-dried residue further comprises using the freeze-dried residue for fertilizer.

11. A method for processing sewage which comprises generally solid components as well as vaporizable components, the method comprising the steps of:

grinding an infeed of sewage into a liquid suspension;

pumping the liquid suspension to boost a line pressure thereof;

providing a freezing atmosphere;

throttling the liquid suspension into the freezing atmosphere that is at a given freezing temperature chosen so that the throttled liquid suspension forms into icy granular particles;

and then, to occur substantially close after the occurrence of that last step of throttling:

drawing a vacuum over the icy granular particles and vaporizing the vaporizable components of the icy granular particles, which disintegrates the generally solid components into a freeze-dried, crumbly residue;

exhausting the vaporizable components to a condenser for extracting a condensate from portions of the vaporizable components, and to extract the other portions of the vaporizable components, which were not condensed, for a given use chosen from one of generating heat and generating electric power; and, removing the freeze-dried residue.

12. The method of claim 11, wherein the step of vaporizing comprises at least one of heating, irradiating, and microwaving.

13. The method of claim 11, further comprising providing a freezer chamber for enclosing the freezing atmosphere, a vacuum chamber in which occurs the step of drawing a vacuum over the icy granular particles, and, means for conveying the icy granular particles from the freezer chamber to the vacuum chamber.

* * * * *